US007804992B2

(12) United States Patent
Wilson et al.

(10) Patent No.: US 7,804,992 B2
(45) Date of Patent: *Sep. 28, 2010

(54) CARDIOVASCULAR RISK ASSESSMENTS USING AORTIC CALCIFICATION INFORMATION DERIVED FROM X-RAY MEASUREMENTS TAKEN WITH A DUAL ENERGY X-RAY DENSITOMETER

(75) Inventors: Kevin Wilson, Waltham, MA (US); Brad Herrington, Andover, MA (US)

(73) Assignee: Hologic, Inc., Bedford, MA (US)

( * ) Notice: Subject to any disclaimer, the term of this patent is extended or adjusted under 35 U.S.C. 154(b) by 968 days.

This patent is subject to a terminal disclaimer.

(21) Appl. No.: 11/542,280

(22) Filed: Oct. 2, 2006

(65) Prior Publication Data

US 2008/0080753 A1 Apr. 3, 2008

(51) Int. Cl.
*G06K 9/00* (2006.01)
(52) U.S. Cl. .................... 382/132; 128/922
(58) Field of Classification Search .................... None
See application file for complete search history.

(56) References Cited

U.S. PATENT DOCUMENTS

| | | | |
|---|---|---|---|
| 7,306,562 B1 | 12/2007 | Baykal | |
| 2003/0215124 A1 | 11/2003 | Li | |
| 2006/0019989 A1 | 1/2006 | Steiner et al. | |
| 2006/0074288 A1* | 4/2006 | Kelly et al. | 600/407 |
| 2007/0248597 A1* | 10/2007 | Henley et al. | 424/133.1 |
| 2007/0274442 A1* | 11/2007 | Gregory et al. | 378/54 |
| 2009/0202572 A1* | 8/2009 | Karsenty et al. | 424/178.1 |

OTHER PUBLICATIONS

Schousboe et al., "Detection of Abdominal Aortic Calcification with Lateral Spine Imaging Using DXA" (see citation provided in Applicants' specification).*
International Search Report and Written Opinion in connection with corresponding International Application No. PCT/US2007/21105.
Hollander, M., et al., *Comparison between measures of atherosclerosis and risk of stroke: the Rotterdam Study*. Stroke, 2003. 34(10): p. 2367.
Kauppila, L.I., et al., *Lumbar disc degeneration and atherosclerosis of the abdominal aorta*. Spine, 1994. 19(8): p. 923-9.
van der Meer, I.M., et al., *Risk factors for progression of atherosclerosis measured at multiple sites in the arterial tree: the Rotterdam Study*. Stroke, 2003. 34(10): p. 2374-9.
Wolffe, J.B. and E.I. Siegal, *X-ray of the abdominal aorta in detection of atherosclerosis*. Clin Med (Northfield Il), 1962. 69: p. 401-6.
Jayalath, R.W., S.H. Mangan, and J. Golledge, *Aortic calcification*. Eur J Vasc Endovasc Surg, 2005. 30(5): p. 476-88.

(Continued)

*Primary Examiner*—Charles Kim
(74) *Attorney, Agent, or Firm*—Cooper & Dunham LLP (57) ABSTRACT

Methods and systems for computer assisted detection of arterial calcification, for example in the abdominal artery, by using measurements such as those conventionally taken with a dual x-ray energy bone densitometers at single energy or dual energy, and for using the calcification assessment either alone or with other information to assess and report a risk of a cardiovascular event.

40 Claims, 5 Drawing Sheets

OTHER PUBLICATIONS van der Meer, I.M., et al., *Predictive value of noninvasive measures of atherosclerosis for incident myocardial infarction: the Rotterdam Study*. Circulation, 2004. 109(9): p. 1089-94.

Wilson, P.W., et al., *Abdominal aortic calcific deposits are an important predictor of vascular morbidity and mortality*. Circulation, 2001. 103(11): p. 1529-34.

JT Schousboe, KE Wilson, and D. Kiel. *Comparison of a Simplified 8-Point Scale (AAC-8) with a Previously Validated 24-Point Scale to Score Abdominal Aortic Calcification With Densitometry or Radiography*. in *ISCD 2006 Annual Meeting*. 2006. San Diego, CA.

Kauppila, L.I., et al., *New indices to classify location, severity and progression of calcific lesions in the abdominal aorta: a 25-year follow-up study*. Atherosclerosis, 1997. 132(2): p. 245-50.

Oei, H.H., et al., *The association between coronary calcification assessed by electron beam computed tomography and measures of extracoronary atherosclerosis: the Rotterdam Coronary Calcification Study*. J Am Coll Cardiol, 2002. 39(11): p. 1745-51.

Witteman, J.C., et al., *Aortic calcified plaques and cardiovascular disease (the Framingham Study)*. Am J Cardiol, 1990. 66(15): p. 1060-4.

Blake, G.M., H.W. Wahner, and I. Fogelman, *Evaluation of Osteoporosis: Dual Energy X-Ray Absorptiometry and Ultrasound in Clinical Practice*. 2nd ed. 1999 Martin Dunitz.

Cooper, J.A., G.J. Miller, and S.E. Humphries, *A comparison of the PROCAM and Framingham point-scoring systems for estimation of individual risk of coronary heart disease in the Second Northwick Park Heart Study*. Atherosclerosis, 2005. 181(1): p. 93-100.

* cited by examiner

| Name: Doe, Jill | Sex: Female | Height: 66.0 in |
| Patient ID: 01 | Ethnicity: Caucasian | Weight: 123.0 lb. |
| DOB: March 28, 1933 | | Age: 66 |

*100*

Scan Information  
Scan Dates: November 18, 1999 and November 18, 1999  
Scan Types: BMD AP Lumbar Spine A0991118BI9  
             SE Lumbar-Thoracic Spine A0991118BI8  
Analysis: November 18, 1999  
Operator: KW  
Model: Delphi SN: 500011  
Comment:  *102*

AP Spine BMD Results: *104*

| Region | Area (cm²) | BMC (g) | BMD (g/cm²) | T-Score | Z-Score |
| --- | --- | --- | --- | --- | --- |
| L1 | 11.41 | 8.11 | 0.710 | -2.0 | -0.6 |
| L2 | 12.22 | 10.26 | 0.840 | -1.7 | -0.2 |
| L3 | 14.55 | 13.63 | 0.936 | -1.3 | -0.3 |
| L4 | 15.38 | 14.24 | 0.926 | -1.7 | -0.1 |
| Total | 53.57 | 46.23 | 0.863 | -1.7 | -0.1 |

Total BMD CV 1.0%, ACF = 1.023, BCF = 1.008, TH = 6.325

*106*  *118*  *118a*

Results of SE Lumbar-Thoracic Spine:

☐ No Vertebral fractures.  
☒ One Vertebral fracture.  *114*  
☐ Two or more Vertebral fractures.

Relative fracture risk based on BMD and one prevalent vertebral fracture is 14.9.  
With HRT treatment, the risk is reduced to 10.3  
With alendronate, the risk is reduced to 7.9  *116*  
The absolute risk of fracture during the next year is 2.4%, 1.7% and 1.3% without treatment, with HRT and with alendronate, respectively.

```
AAC score  4
CV risk score 15      } 120
Guideline  5
```

Physician's Comment:  
L2 wedge deformity.

Reference curve and scores matched to White Female    (Other Reported Information) - *122*

CARDIOVASCULAR RISK ASSESSMENTS USING AORTIC CALCIFICATION INFORMATION DERIVED FROM X-RAY MEASUREMENTS TAKEN WITH A DUAL ENERGY X-RAY DENSITOMETER

FIELD AND BACKGROUND

This patent specification is in the field of methods and equipment for assisting medical professionals in assessing cardiovascular risk of patients and bone condition and fracture risk of patients. More particularly, this patent specification pertains to taking x-ray measurements with a dual energy bone densitometer for at least one of the two x-ray energy ranges that the densitometer can measure, and processing these measurements to detect and quantify aortic calcification, to use the results in estimating cardiovascular risk, and to report the outcome in particularly useful ways.

The abdominal aorta is a large, fluid filled vessel comprised of soft tissue. It can be barely visible on conventional x-ray images and is typically is visualized with the use of a radio-opaque contrast material. A vessel that is calcified usually presents with a linear or eggshell calcified pattern which is typical of calcification in the wall of a fluid filled structure. The history of using radiographs to identify abdominal aortic calcifications is well-established [1,2,5,11,14,15,16]. (The superscript numerals refer to the documents cited at the end of the detailed description; all of those cited documents are hereby incorporated by reference in this patent specification.) A recent (2005) review article of methods for detection of abdominal aortic calcifications describes three primary methods: plain radiograph, ECT, and CT. It concludes, "Presently no modality has been accepted as the gold standard for the measurement of abdominal aortic calcification," [5] but observes that "The simplest method of detecting abdominal aortic calcification is with plain abdominal X-ray." [5]

Abdominal Aortic Calcification (AAC) is seen anterior to the lumbar spine in lateral view and is graded in severity by several methods[8-10] related to the length of the AAC seen in the image. The published literature indicates a graded association between the length of the AAC seen in the image and the risk of future morbidity and mortality.[1,3,6,7] In a typical grading scheme, the posterior and anterior walls of the aorta are graded in the area in front of the L1-L4 vertebra for total length of calcifications seen. For example, $0, \leq 1$ cm, 1 to 2.4 cm, 2.5 to 4.9 cm, $\geq 5$ cm is considered, absent, dubious, mild, moderate, and severe, respectively.[10] It has been reported that AAC is diagnostic for arteriosclerosis[1-4]. AAC is believed to be strongly associated with a number of diseases, independent of traditional clinical risk factors such as age, cigarette use, diabetes mellitus, systolic blood pressure, left ventricular hypertrophy, body mass index, cholesterol, and HDL cholesterol.[1,3,5-7] The known literature identifies plain radiography, CT and ECT as the modalities to be used for AAC detection and quantification. MRI is also referenced as a modality in connection with assessing atherosclerosis.[23]

A different modality, dual x-ray energy bone densitometry, has long been used for other purposes, mainly to obtain bone condition assessment information, including the projected bone mineral density (BMD, in $g/cm^2$) at various anatomical sites, using dual energy x-ray absorptiometry (DXA) techniques that do not involve CT scanning such as in qCT (quantitative CT). One example of DXA systems is available from Hologic, Inc. of Bedford Mass. under the trade name Discovery. It has an examination table and a C-Arm at opposite ends of which are mounted an x-ray tube and a multi-detector array. The patient is positioned on the examination table between the x-ray tube and the detector array of the C-arm. For the assessment of bone mineral density, a fan-shaped beam of x-rays from the tube and the detector are scanned as a unit axially along the patient, while the x-rays are alternatively pulsed at high and low energy ranges. By comparing the relative attenuation of the x-rays at the two energies, the contributions to the attenuation due to the soft tissue can be subtracted. In other equipment, dual energy x-ray measurements are obtained by using a steady x-ray beam of relatively broad energy range impinging on two sets of detectors that measure respective energy ranges of the beam. At least in principle, similar results may be obtained without scanning, using an x-ray beam of a sufficient cross-section and a 2D array of detector elements. In each case, an image can be obtained of the bony structure of the body by the soft-tissue subtraction method. This image is then input into BMD analysis, which calculates and reports the BMD. The image can be displayed by showing it on a screen and/or printing it and can be stores in PACS or other storage/retrieval systems together with other densitometry and patient data.

When the patient's spine is scanned with a dual energy densitometer, the displayed image is similar to that in conventional spine radiography except that it requires many times less x-ray exposure and the entire spine or any desired part thereof can be scanned in one pass and shown as a single image. The image can be derived from measurements at both x-ray energy ranges or at one of them (single energy image). In the case of systems such as the Discovery, a single energy image can be obtained by selecting a fixed, relatively narrow energy range rather than alternating between two energy ranges. If a dual energy image is already available but a single energy image is desirable for some reason, it can be extracted simply by using only the x-ray detector outputs for one of the energies. In systems that use two sets of x-ray detectors, a single energy image can be extracted by using only the output of only one of the detector sets.

One of the options for densitometers offered by Hologic, Inc. is available under the trade name Instant Vertebral Assessment (IVA), sometimes referred to as vertebral fracture assessment (VFA), wherein vertebral deformities can be evaluated either quantitatively or visually, similar to standard quantitative and visual conventional radiograph or CT reading methods. IVA images are lateral spine images typically taken at single energy. While the images produced using x-ray bone densitometry IVA are not of sufficient quality for general radiological use, it has been observed that the quality of IVA images is similar to that of abdominal radiographs for visualizing abdominal aorta calcifications. In fact, AAC can be seen in DXA images sufficiently well to have allowed the Food and Drug Administration (FDA) to clear (510K clearance K060111 approval Apr. 24, 2006) Hologic Inc. for visualizing AAC with its DXA equipment.

SUMMARY OF DISCLOSURE

This systems and method disclosed in this patent specification generally relate to automatic detection of AAC using a dual x-ray energy bone densitometer and to using computer assisted grading of AAC for computer assisted estimation of a risk of a cardiovascular event, such as heart attack and stroke, with or without combining the AAC information with traditional clinical risk factors to better estimate the patients risks of cardiovascular event. The results are reported either alone or in combination with other results from the DXA scan. Preferably, AAC is assessed from a single energy lateral view. It can also be assessed from a dual energy lateral image. A single energy image can be obtained in much shorter time and at lower x-ray dose, while a dual energy image can require higher dose and longer acquisition time but lessen some effects of soft tissue. For example a densitometer such as the Discovery can acquire a single energy lateral image of vertebrae T4 to L4 in about 10 seconds but can take several times that for a similar dual energy image. Dual energy images can be used instead if the longer scan time and higher dose are justified or already available, and in the case of bone densitometers that use a wide energy range in the x-ray beam and separate the two energies at the detector system. It should be understood that the term single energy is used in this patent specification to refer to an x-ray energy range rather than to a single value of the energy spectrum, and the term dual energy refers to two ranges of x-ray energy ranges that may partly overlap A non-limiting example of a method disclosed in this patent estimates a patient's risk of a cardiovascular event using aortic calcification information obtained through dual x-ray energy bone densitometry and reports the estimated risk as well as bone assessment information. The method comprises obtaining x-ray measurements of a patient's anatomy that includes a selected portion of the patient's aorta, wherein the measurements can be single energy or dual energy and the measurements typically comprise a lateral view of the patient, deriving digital image information describing an image of at least the selected portion of the patient's aorta by computer processing that uses the x-ray measurements, producing aortic calcification information describing at least one selected calcification property of the selected portion of the aorta by computer processing that uses the digital image information, estimating cardiovascular risk information indicative of an assessment of risk of a cardiovascular event by computer processing that uses the aortic calcification information, calculating bone assessment information by computer processing using the digital image information, and reporting the estimated cardiovascular risk information and a record of derived bone assessment information, with or without also reporting other risk factors for the patient, such as cholesterol levels, blood pressure, body fat information, previous cardiovascular events, etc. The report can be shown by displaying it on a computer screen, printing it, storing it in a server or sending it electronically to a remote location, and/or otherwise. In the case of using single energy lateral view, the bone assessment can be a vertebral fracture assessment or another type of morphometry assessment, while in the case of using a dual energy lateral view the bone assessment can additionally include bone mineral content or density information, while in the case of additionally taking an AP (anterior-posterior or posterior-anterior) view the bone assessment can additionally include information related to bone mineral content or density derived from that view.

A non-limiting example of a system disclosed in this patent application comprises a dual x-ray energy bone densitometer that obtains x-ray measurements of a patient's anatomy that includes a selected portion of the patient's aorta. The x-ray measurements can be at a single energy or dual energy and can typically come from a lateral view of the patient. A computer is coupled with the densitometer to receive the x-ray measurements and process them to derive digital image information describing an image of at least the selected portion of the patient's aorta. The computer is further programmed to process the digital image information to produce aortic calcification information describing at least one selected calcification property of the selected portion of the aorta, and is further programmed to process the aortic calcification information to estimate cardiovascular risk information indicative of an assessment of risk of a cardiovascular event for the patient. The system further includes a reporting unit such as a display coupled with the computer to receive the cardiovascular risk information and show it on a screen and/or otherwise report it. A further non-limiting example is a computer program product that can be loaded as an application program in a computer to carry out examples of the disclosed method.

DETAILED DESCRIPTION OF PREFERRED EMBODIMENTS

Figure 1:
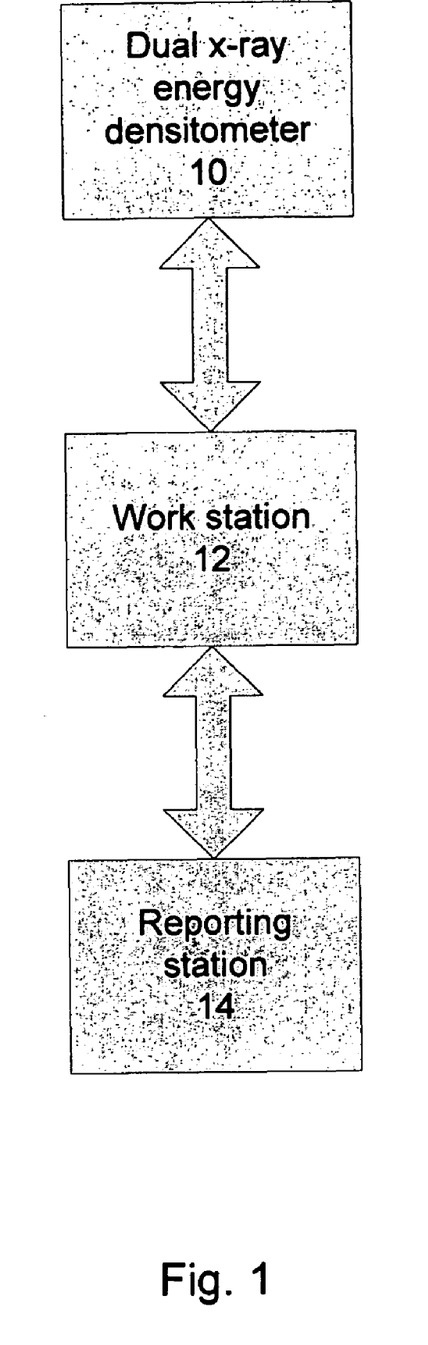
FIG. 1 illustrates in block diagram form one example of the main components of a system that estimates and reports risk of a cardiovascular events using dual x-ray energy bone densitometry (DXA) data.

Referring to FIG. 1, the main components of a system carrying out one example of the disclosed method of estimating and reporting a risk of a cardiovascular event are a dual x-ray energy bone densitometer 10, a processing workstation 12, and a reporting station 14. Densitometer 10 can be the scanning and pre-processing part of a device such as disclosed in U.S. Pat. No. 6,385,283, which is hereby incorporated by reference, or the densitometer available from Hologic, Inc. under the trade name Discovery and equipped with appropriate software including IVA software. Its purpose here is to obtain x-ray measurements of patient's anatomy that includes the appropriate part of the aorta, for example the portion of the abdominal aorta anterior to the lumbar spine. While information for similar processing can be derived from conventional radiography systems, or CT systems, or ECT systems, it is believed that using dual x-ray densitometry is particularly advantageous at least because it exposes the patient to a much lower radiation dose than these other modalities, is much less expensive than CT or ECT, and can be done with the raw data that already has been generated for use in bone assessment. When densitometer 10 uses an x-ray beam alternating between high and low energies, as in the Discovery system, the x-ray measurements used in this example can be single energy measurements for a lateral view. As noted above, in the alternative single energy images can be extracted from dual energy measurements. Single energy x-ray measurements from DXA can also be used for bone assessment such as IVA or vertebral fracture assessment. In the alternative, the x-ray measurements can be dual energy measurements, obtained with DXA equipment with an x-ray beam alternating between two energies or with a scanning densitometer that uses an x-ray beam with a wider energy range and two sets of detectors, or with another type of densitometer. When dual energy measurements are available, they can be used for additional or alternative bone assessment information, such as information regarding bone mineral content or density. The x-ray measurements for AAC typically are acquired from a lateral view of the patient, while those for additional or alternative bone assessment can be acquired in a lateral or other views such as an AP view.

After conventional initial processing the x-ray measurements are delivered to workstation 12 that has one or more computers programmed to carry out known processing to derive digital image information such as, but not limited to, pixel values describing a single-energy and/or a dual-energy image of the patient's anatomy and bone assessment information. One example of a workstation with that functionality is the workstation disclosed in said patent U.S. Pat. No. 6,385,283 or that of the Discovery system. In addition, workstation 12 is programmed to carry new steps in which it processes the digital image information to produce aortic calcification information regarding a selected portion of the patient's aorta, and is programmed to use the result to estimate cardiovascular risk information. The output of workstation 12 is delivered to reporting station 14 that can include one or more computer screens for displaying the results from workstation 12, printing equipment, magnetic and optical disc drives for longer term storage of those results and other data, communication facility to transfer the results and other data to remote locations and storage such as PACS, etc.

Figure 2:
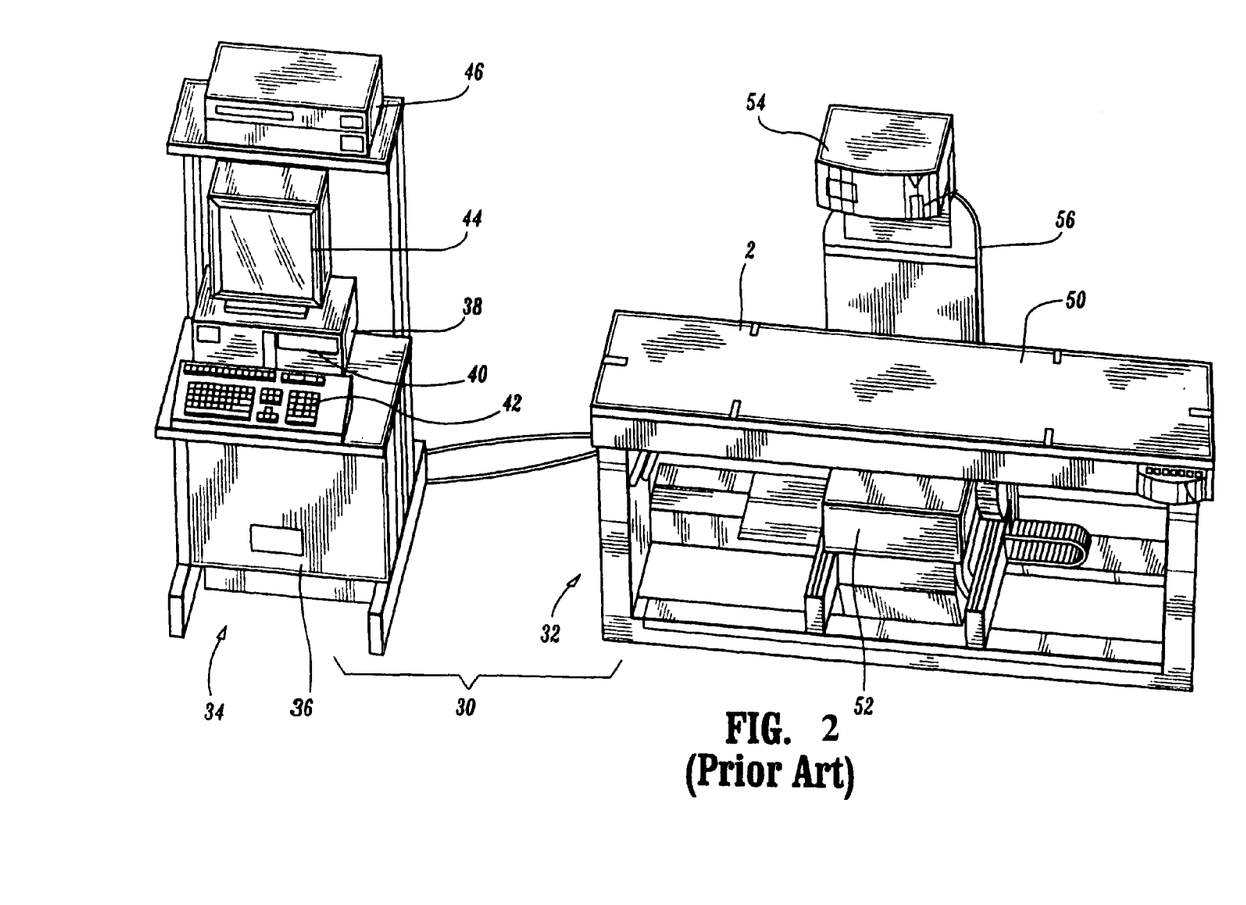
FIG. 2 illustrates a prior art DXA scanning systems that can generate and process DXA data if programmed to carry out the process disclosed in this patent specification.

FIG. 2 illustrates in greater detail a known x-ray bone densitometer system with facilities that can be used to practice the methods disclosed in this patent specification. It includes a scanning system 30 that comprises a patient table unit 32 with a patient table 50 and a C-arm 56 serving as a source-detector support. A workstation 34 controls patient table unit 32 and C-arm 56 and processes scan data into quantitative bone assessment information such as BMD, images, and IVA information. Workstation 34 includes a power supply module 36, one or more host computers 38 with a mass data storage devices 40, an operator console keyboard 42, a display monitor 44 and a printer 46. Table 50 can move up and down and along its long dimension and may also move along its short dimension. C-arm 56 also moves along the length of table 50 to scan a patient thereon with a fan-shaped beam of x-rays from source 52 so that a detector array 54 and associated electronics can produce dual energy or single energy scan data. The C-arm may also be able to move across the table. For the purposes of carrying out the method disclosed in this patent specification, different densitometry systems can be used so long as they can do a lateral scan of a patient and obtain the requisite single energy and/or dual energy x-ray measurements of the appropriate aortic portion. They can range from a basic model in which the C-arm does not rotate so that the lateral scan needs to be done in the decubitus position, and the table has limited range or motions or no motion, to the most sophisticated models that have many more features and in which the lateral scan can be done either in the supine or in the decubitus positions. One of the features that some of the known x-ray bone densitometry systems have is software that either completely automatically or with some operator input identifies specified Regions Of Interest (ROI) such as vertebral bodies or other bone structures such as the femur head. See, for example, U.S. Pat. Nos. 5,850,836 and 5,228,068 that pertain to morphometry processes that identify vertebral bodies and U.S. Pat. No. 6,853,741 that pertains mainly to the femur head; all three patents are hereby incorporated by reference in this patent specification. Morphometry option and IVA options have long been available from Hologic, Inc. for its x-ray bone densitometers.

When used for carrying out a method disclosed in this patent application, units 2, 32, 50, 52, 54, and 56 of FIG. 2 can serve as an example of densitometer 10 of FIG. 1; units 34, 36, 38, 40 and 42 can serve as and example of workstation 12 of FIG. 1; and units 40 and 46 can serve as an example of reporting station 14 of FIG. 1.

Figure 3:
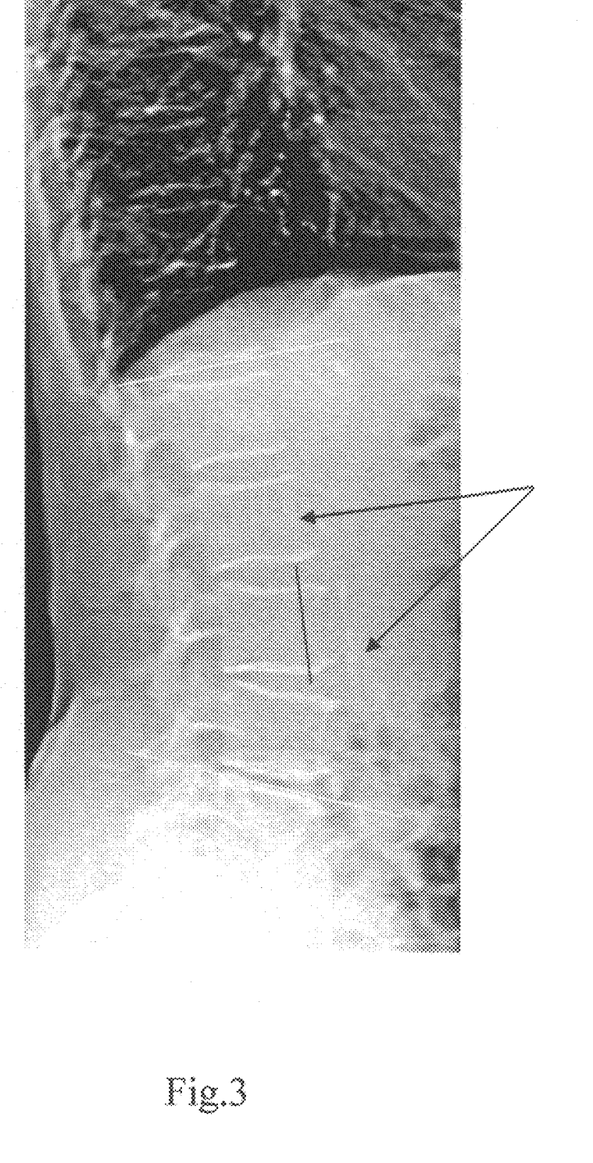
FIG. 3 illustrates a single energy lateral DXA image showing aortic calcification in the lumbar aorta.

FIG. 3 illustrates a single energy lateral image from a dual x-ray energy densitometer. AAC can be seen anterior of lumbar vertebrae L2 and L3. Various parameters of this AAC can be detected with computer assistance such as its length along the aorta either in absolute units or in units scaled to the height of the laterally adjacent vertebral bodies, its area in the image, its bone mineral content (BMC) in units such as those commonly used in DXA, it areal density of calcification, or other parameters related to the degree and nature of the detected calcification. While FIG. 3 illustrates a single energy image, dual energy images can be used instead or in addition to detect and assess AAC parameters that may be comparably or better visualized in dual energy imaging. The lines through intervertebral spaces in FIG. 3 delineate the lumbar vertebrae. It is important that DXA images such as that in FIG. 3, which typically are produced when using the IVA procedure, show the thoracic region as well as the lumbar region in a single image, which it typically not the case with conventional radiographs. Accordingly, the same DXA image information can be used to detect and assess thoracic arterial calcification (TAC) in addition to or instead of abdominal arterial calcification and to use the resulting information in assessing and reporting risk of cardiovascular events.[11]

The detection of AAC and/or TAC can be through a computer assisted process that is entirely automated or involves some participation by the health care professional. In an entirely automated process, a computer search algorithm evaluates the image information, for example by testing pixel values of a pixel-based image to identify pixel clusters that match criteria indicative of aortic calcification. Because calcification can be somewhat patchy, the algorithm can be made to add up clusters that individually suggest calcification but are not contiguous. Constraint can be imposed on such adding up, such as requirements that the clusters have minimum size, that they be within a specified area, that they be spaced by no more than a specified distance, etc. The search algorithm can first identify the vertebral bodies, for example using the commercially available CADfx software from Hologic, Inc., and then search an ROI that is preset to encompass a specified area relative to the vertebral bodies in the image, for example an area within a specified distance anterior from the lumbar and/or thoracic vertebrae in a lateral view. The distance may be expressed as absolute units or in units of vertebral size for the particular patient. Various search algorithms can be used; as a non-limiting example an algorithm may select as AAC pixels those that have pixel values exceeding a threshold and possibly meeting additional criteria such as comparison with adjacent pixels. As a non-limiting example, the threshold can be based on an average of all pixels in the searched ROI or on a histological value related to pixel values in the ROI or in other regions of the image. More sophisticated search algorithms can be used as an alternative, using techniques such as those disclosed in U.S. Pat. No. 6,138,045, hereby incorporated by reference herein, and the patents cited at column 1, lines 25-40 thereof, also incorporated by reference herein. As yet another alternative, image marking by a health professional can assist in the computer identification of the ROI to be searched. For example, by using a mouse of another input device, the health professional can mark the image such as by drawing an outline around the relevant portion of the aorta, or by marking the vertical ends of the AAC visible in the image, or by outlining the AAC, or in some other way, and the search algorithm can then use the marking information to select the ROI and/or to otherwise use the marking information in identifying AAC parameters. As yet another alternative, the function of the search algorithm can be limited to calculating the distance between marks designating the vertical ends of the AAC portion, or to calculating the AAC area outlined by the health professional. As noted above, the result of this process is aortic calcification information that can include one or more parameters such as the length of the calcified portion in appropriate units along the length of the pertinent aortic portion, the area of calcification, the BMC of the calcification, the areal density of the calcification (BMC/area of calcification), and possible other parameters. Parameters such as the amount of calcification are calculated using dual energy image information rather than a single energy image, in the manner currently used in commercial dual x-ray energy bone densitometers, and in units such as grams of calcium hydroxyapetite equivalent. Both the total amount of aortic calcification and the area and/or length of the calcification can be predictive of disease and its severity and can be used in arterial calcification grading schemes, for example schemes such as those proposed in the cited articles. The aortic calcification information calculated or estimated in this manner can be presented as digital data quantifying the estimates and/or by way of grading results, for example 5 grades or 8 grades or some other number of grades indicative of the degree and/or nature of calcification and based on the estimated parameters alone or in combination with other factors such as clinical information regarding the patient and possibly input from a health professional.

Arterial calcification information derived in this manner is used as an input to a computer assisted process in workstation 12 that calculates or estimates cardiovascular risk information, possibly also based on additional factors such as clinical data input by a health professional or available from another source and possible other data such as normative data for patient populations relevant to the patient being examined. In a simplified example, if a numerical scoring system of 8 grades is used in the assessment of arterial calcification, each grade can be related through a look-up table to a respective grade of risk of cardiovascular event or to a probability of such event in a specified time period. The look-up table can be based on current knowledge or such relationship or on normative data derived in known manner from examining a historical base of images showing arterial calcification and relating them to actual occurrence of cardiovascular events in the patient population. Additional or alternative statistical studies and approaches can be used in creating and refining the look-up table. Such techniques have been used in creating, for example, the ATP III Guidelines At-A-Glance Quick Desk Reference available from the National Institute of Health, National Heart, Ling and Blood Institute[21], that relates a set of factors such as cholesterol level, cigarette smoking, hypertension and others to level of coronary heart disease (CHD). The arterial calcification information can be one of the factors that go into the CHD guidelines, hereby incorporated by reference. Alternatively, the arterial information can be used by itself to produce cardiovascular risk information such as, but not limited to, a numerical or otherwise quantified grade of risk. Still alternatively, the arterial calcification information can be used to estimate cardiovascular risk information when combined with clinical information regarding the patent and/or other information entered into the process by a health professional or available from another source, to estimate risk information in a manner similar to that in said guidelines. The cardiovascular risk information can then be used to help the health professional assess and treat the patient, and can additionally be used as an entry to a process that automatically produces recommended treatment choices, again in the manner done in said guidelines. The term cardio-vascular risk information is used in this patent specification in a broad sense, and can be a score such as in the CHD Guidelines or to other information that pertains to risk associated with the patient's cardiovascular system.

Figure 4:
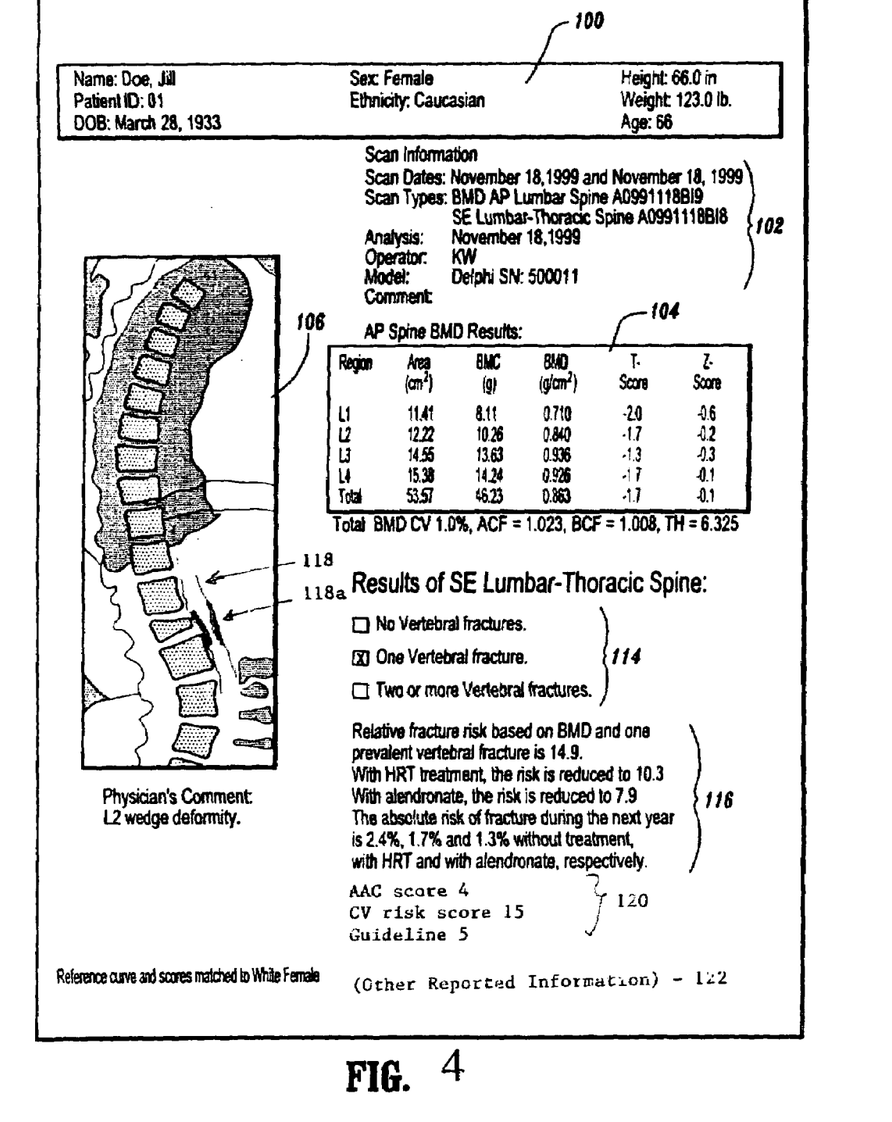
FIG. 4 illustrates a non-limiting example of a display of bone assessment information and of cardiovascular risk information derived at least in part from DXA measurements.

The risk information and if desired the arterial calcification information and other information can be reported in any number of ways. As a non-limiting example, it can be added to a report such as illustrated in FIG. 2 or FIG. 3 of said U.S. Pat. No. 6,385,283. One example of such combined report is illustrated in FIG. 4 in this patent specification, which contains all of the information illustrated in FIG. 3 in the patent and, additionally, illustrates an image of an artery 118 that has a calcified portion 118a and adds cardiovascular risk related information 120. FIG. 4 is a drawing rather than an actual DXA image (as is FIG. 3 herein). As seen in FIG. 4, information 120 comprises an entry "AAC score 4" that indicates the degree and nature of detected arterial calcification according to an example of a grading scheme, an entry "CV risk score 15" that indicated the cardiovascular risk grade according to an example of another grading scheme, and an entry "Guideline 5" referring to an example of a treatment guideline that relates the patient's CV risk score to a suggested treatment or choice of treatments according to a guideline similar in principle to said NIH guideline. Of course, this is only an illustrative example of entries 120, and more or less information related to AAC and cardiovascular risk can be displayed. As an alternative, some or all of the information such as that displayed at 120 can be displayed by itself, without some or all of the other information seen in FIG. 4. In such case, information such as at 120 can be displayed alone (or with image 106) by itself on a computer screen, and possibly but not necessarily concurrently with a separate display of bone assessment information such as that seen in FIG. 4. In addition, the report can include and selectively display other reported information 122, for example clinical information about the patient such as cholesterol levels, information regarding previous cardiovascular events, regarding blood pressure, weight and height, etc.

Figure 5:
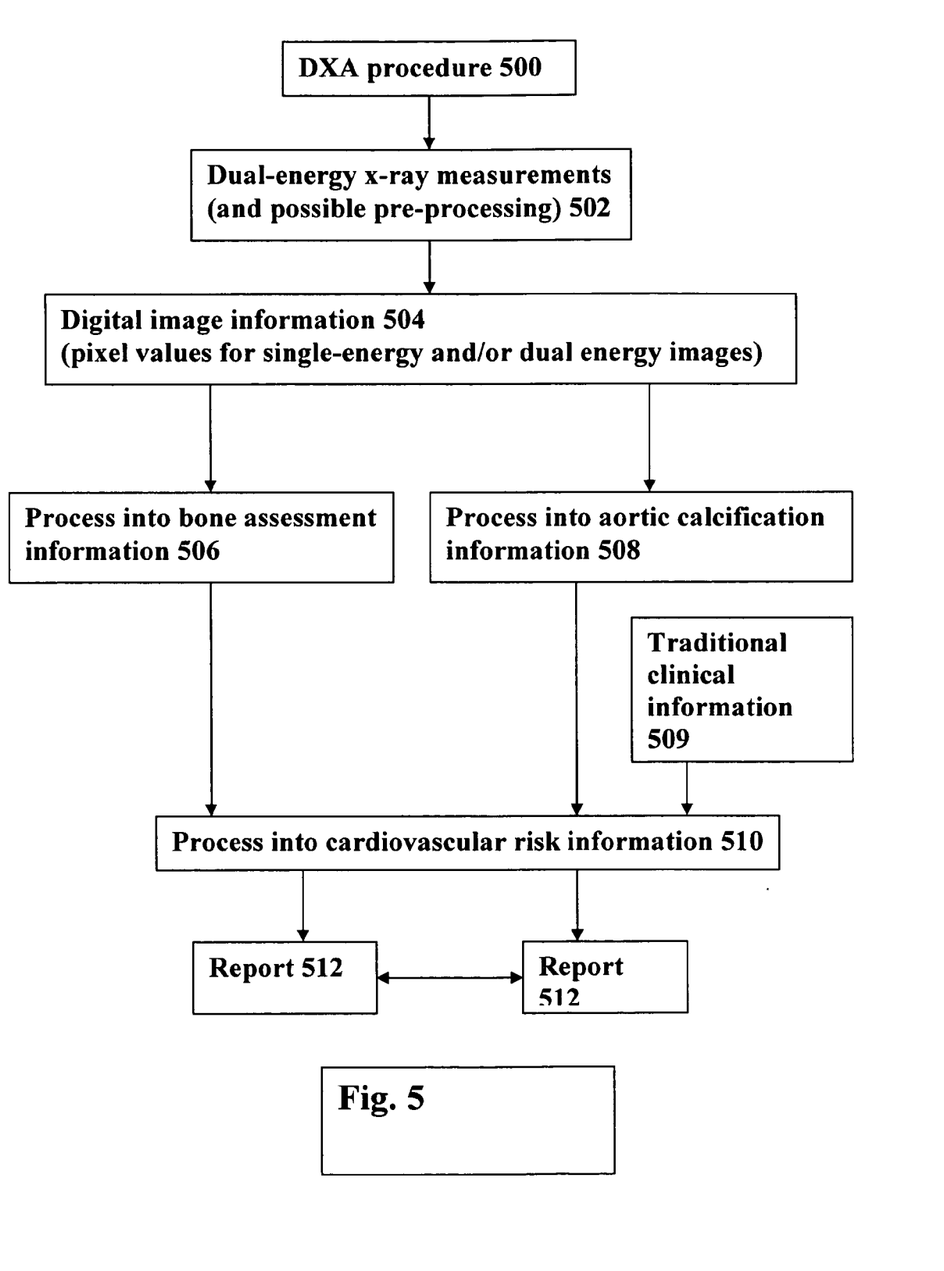
FIG. 5 illustrates process components of a method for generating results such as those in FIG. 4.

FIG. 5 illustrates an example of main components of a process according to the disclosure above. Process component 500 is a DXA procedure that obtains single energy and/or dual energy x-ray measurements of a patient's anatomy that includes a selected portion of a patient's aorta, preferably in a lateral view and in desired in an AP view as well. Component 500 can carry out conventional pre-processing of the x-ray measurements, or can deliver raw measurements. Process component 502 receives the x-ray measurement information from component 500 in digital form, typically in the form of information describing the value and position of each image pixel for the single energy or for each of two x-ray energies, applies any necessary conventional pre-processing thereto, such as dark current correction and other corrections, and derives digital image information that describes an image of at least the pertinent portion of the aorta but more typically an image such as 106 in FIG. 4, as a single energy image or a dual energy image. The image information can be in the form of pixel data containing a pixel value for each respective pixel of a single energy image and/or the processed dual energy image that effectively eliminates soft tissue but leaves bone and calcification in the image. The images in this case can be the same as available in conventional DXA and/or IVA or they can be optimized for visualizing and/or detecting arterial calcification using known techniques. Process component 506 uses the output of component 504 in the manner known in conventional DXA to generate bone assessment information such as BMD and/or IVA and to provide it to one or more reporting components 512 in the conventional manner. Process component 508 is unique to the process disclosed in this patent specification and receives image information from component 504 to process it according to the principles discussed above to thereby produce aortic calcification information. As discussed above, in a simplified example the output of process component 508 can be only a grade of calcification, but alternatively it can include additional and more detailed digital information defining arterial calcification parameters such as a measure of the vertical extent of calcification, area of calcification, etc. Process component 510 uses the arterial calcification information from component 508 in a computer assisted process that estimates cardiovascular risk information, for example a patient's risk of a cardiovascular event, according to the principles discussed above. The estimate can be based solely on the arterial calcification information from component 508 or it can additionally use traditional clinical information that process component 509 provides. The clinical information can be patient age and other patient information of the type that goes into the process outlined in said NIH guidelines, and/or it can include additional clinical observations of a health care professional applicable to patient being examined. The output of process component 510 goes to one or more reporting components 512. A reporting component 512 can display the appropriate information, it can store it for future use, direct it to a remote location, print it, or otherwise utilize it. A reporting component 512 can display or otherwise utilize only bone assessment information, or only cardiovascular risk information, or any desired combination of sub-combination of each. In addition, process component 510 can generate recommended treatment information and supply it to one or more reporting components 512 for display or other use.

There exist 10-year cardiovascular risk scores, for example the Framingham Point Score or PROCAM[13] risk score. These measure clinical risk factors for cardiovascular risk. Since AAC is independent of these risk factors, the additional risk from AAC grade/score can be used to more accurately calculate an individual's risk. For example, the computer can calculate the Framingham Point Score from inputs (age, total cholesterol, HDL, Systolic BP, gender) or the Framingham Point score could be directly entered for the patient. The computer can combine this risk score with the additional relative risk conferred by the AAC grade/score to obtain a 10 year risk that more accurately reflects the individual's risk. This is useful because various treatment guidelines (http://www.nhlbi.nih.gov/guidelines/cholesterol/atglance.pdf) are available that depend on the individuals 10 year cardiovascular risk score. The treatment guidelines for the level of risk calculated can also be included in the report.

CITATIONS TO MATERIAL INCORPORATED BY REFERENCE IN THIS PATENT SPECIFICATION

1. Hollander, M., et al., *Comparison between measures of atherosclerosis and risk of stroke: the Rotterdam Study*. Stroke, 2003. 34(10): p. 2367-72.
2. Kauppila, L. I., et al., *Lumbar disc degeneration and atherosclerosis of the abdominal aorta*. Spine, 1994. 19(8): p. 923-9.
3. van der Meer, I. M., et al., *Risk factors for progression of atherosclerosis measured at multiple sites in the arterial tree: the Rotterdam Study*. Stroke, 2003. 34(10): p. 2374-9.
4. Wolffe, J. B. and E. I. Siegal, *X-ray of the abdominal aorta in detection of atherosclerosis*. Clin Med (Northfield Ill.), 1962. 69: p. 401-6.
5. Jayalath, R. W., S. H. Mangan, and J. Golledge, *Aortic calcification*. Eur J Vasc Endovasc Surg, 2005. 30(5): p. 476-88.
6. van der Meer, I. M., et al., *Predictive value of noninvasive measures of atherosclerosis for incident myocardial infarction: the Rotterdam Study*. Circulation, 2004. 109(9): p. 1089-94.
7. Wilson, P. W., et al., *Abdominal aortic calcific deposits are an important predictor of vascular morbidity and mortality*. Circulation, 2001. 103(11): p. 1529-34.
8. J T Schousboe, K E Wilson, and D. Kiel. *Comparison of a Simplified 8-Point Scale (AAC-8) with a Previously Validated 24-Point Scale to Score Abdominal Aortic Calcification With Densitometry or Radiography*. in ISCD 2006 Annual Meeting. 2006. San Diego, Calif.
9. Kauppila, L. I., et al., *New indices to classify location, severity and progression of calcific lesions in the abdominal aorta: a 25-year follow-up study*. Atherosclerosis, 1997. 132(2): p. 245-50.
10. Oei, H. H., et al., *The association between coronary calcification assessed by electron beam computed tomography and measures of extracoronary atherosclerosis: the Rotterdam Coronary Calcification Study*. J Am Coll Cardiol, 2002. 39(11): p. 1745-51.
11. Witteman, J. C., et al., *Aortic calcified plaques and cardiovascular disease (the Framingham Study)*. Am J Cardiol, 1990. 66(15): p. 1060-4.
12. Blake, G. M., H. W. Wahner, and I. Fogelman, *Evaluation of Osteoporosis: Dual Energy X-Ray Absorptiometry and Ultrasound in Clinical Practice*. 2nd ed. 1999 Martin Dunitz
13. Cooper, J. A., G. J. Miller, and S. E. Humphries, *A comparison of the PROCAM and Framingham point-scoring systems for estimation of individual risk of coronary heart disease in the Second Northwick Park Heart Study*. Atherosclerosis, 2005. 181(1): p. 93-100.
14. Schousboe, J. T., Wilson, K. E., Kiel, D. P., *Detection of Abdominal Aortic Calcification With Lateral Spine Imaging Using DXA*, Journal of Clinical Densitometry, vol. 9, no. 3, 302-308, 2006.
15. Witteman J C M, Van Saase J L C Valkenburg H A, *Aortic Calcification as a predictor of cardiovascular mortality*, Lancet 1986; 2:1120-2.
16. Witteman J C M, Grobbee D E, Valkenburg H A, van Hemert A M, Stijnen T, Hofman A, *J-shaped relation between change in diastolic blood pressure and progression of aortic atherosclerosis*, Lancet 1994. 343:504-7.
17. Wilson K E, *Detection of Abdominal Aortic Calcification with IVA*, Hologic, Inc. publication W-158 US/INTL May 2006.
18. Kauppila L I, et al., *Disc Degeneration/Back Pain and Calcification of the Abdominal Aorta: A 25-Year Follow-Up Study in Framingham*, Spine: vol. 22(14) 15 Jul. 1997, 1642-1647.
19. Schousboe K. E., Kiel D. P., *Detection of Abdominal Aortic Calcification With Lateral DXA Scans*, presented at ISCD 2006 Annual Meeting February 1-4, San Diego, Calif.
20. Tanko L B, et al., *Relationship Between Osteoporosis and Cardiovascular Disease in Postmenopausal Women*, J Bone & Min Res, vol. 20, no 11, 2005, 1912-1920.
21. ATP III Guidelines At-A-Glance Quick Desk Reference, NIH Publ. No. 01-3305, May 2001.
22. de Leeuw F E, et al., *Aortic Atherosclerosis at Middle Age Predicts Cerebral White Matter Lesions in the Elderly*, Stroke, February 2000, 425-429.

23. Raevan P D, et al., *Coronary artery and abdominal aortic calcification are associated with cardiovascular disease in type 2 diabetes*, Diabetologia (2005) 48:379-385.
24. Tanko L B, et al., *Effective doses of ibandronate do not influence the 3-year progression of aortic calcification in elderly osteoporotic women*, Osteoporosis In (2005) 16:184-190.
25. Walsh G R, et al., *Abdominal aortic calcific deposits are associated with increased risk for congestive heart failure: The Framingham Heart Study*, Am Heart J, October 2202, 733739.
26. Bagger Y Z, et al., *Radiographic measure of aorta calcification is a site-specific predictor of bone loss and fracture risk at the hip*, J Int Med 2006; 259:598-605.
27. Wilson P W F, et al., *Abdominal Aortic Calcific Deposits Are and Important Predictor of Vascular Morbidity and Mortality*, Circulation Mar. 20, 2001, 1529-1534.

The invention claimed is:

1. A computer-implemented method of estimating cardiovascular risk information for a patient using aortic calcification information obtained with a dual x-ray energy range bone densitometer and generating a record of the estimated risk together with a record of bone assessment information, comprising:
   obtaining dual energy range x-ray measurements of a patient's anatomy that includes a selected portion of the patient's aorta, by using a dual energy range bone densitometer;
   deriving digital image information describing an image of at least the selected portion of the patient's aorta, by computer processing that uses said x-ray measurements;
   producing aortic calcification information describing at least one selected calcification property of the selected portion of the aorta, by computer processing that uses the digital image information;
   estimating cardiovascular risk information related to an assessment of risk of a cardiovascular event by computer processing that uses the aortic calcification information;
   calculating first bone assessment information, by computer processing that uses the digital image information; and
   reporting the estimated cardiovascular risk information and the calculated bone assessment information.

2. A method as in claim 1 including inputting additional information regarding clinical risk factors for the patient and using said additional information in said estimating of cardiovascular risk information.

3. A method as in claim 1 including showing an image of the patient's anatomy derived using said digital image information, together with the cardiovascular risk assessment and bone assessment information.

4. A method as in claim 1 in which the calcification information comprises a grade calculated according to a selected grading scheme.

5. A method as in claim 1 in which calcification property is at least one of length of a calcified portion of the aorta, area of the calcified portion, mineral content of the calcified portion, and mineral content per unit area of the calcified portion.

6. A method as in claim 1 in which said reporting comprises concurrently showing the cardiovascular risk information and the bone assessment information.

7. A method as in claim 1 in which said reporting comprises showing the cardiovascular risk information and the bone assessment information at different times.

8. A method as in claim 1 in which said reporting comprises showing the cardiovascular risk information and the bone assessment information at a single display or document.

9. A method as in claim 1 in which said reporting comprises showing the cardiovascular risk information and the bone assessment information at separate display screens or documents.

10. A method as in claim 1 in which the producing comprises scaling aortic calcification information to patient's vertebral size information.

11. A method as in claim 1 in which the obtaining comprises obtaining the x-ray measurements from a lateral view of the patient.

12. A method as in claim 11 the deriving comprises processing the lateral view measurements, and further including obtaining dual energy range AP x-ray measurements from an AP view of the patient and computer processing the AP measurements to derive and report second bone assessment results that include indications of BMD and/or BMC.

13. A method as in claim 1 in which the selected portion of the aorta comprises a selected portion of the abdominal aorta.

14. A method as in claim 1 in which the selected portion of the aorta comprises a selected portion of the thoracic aorta.

15. A computer-implemented method comprising:
   using a processor to perform steps comprising:
   obtaining dual energy range x-ray measurements of a patient's anatomy that includes a selected portion of the patient's aorta, by using a dual x-ray energy range bone densitometer system;
   using the x-ray measurements to derive digital image information describing an image of at least the selected portion of the patient's aorta;
   producing aortic calcification information describing at least one selected calcification property of the selected portion of the aorta, by computer processing that uses the digital image information;
   estimating cardiovascular risk information related to an assessment of risk of a cardiovascular event by computer processing using the aortic calcification information; and
   reporting the calculated cardiovascular risk information.

16. A method as in claim 15 in which the digital image information describes values of image pixels, and the producing of aortic calcification information comprises applying at least one selected computer search algorithm to the digital image information to identify pixel groupings that meet selected pixel value characteristics.

17. A method as in claim 16 including displaying an image of the patient's anatomy, including an image of the selected portion of the aorta, derived from said digital image information, and manually marking a calcified portion of the aorta visible in the image, wherein the producing of aortic calcification information comprises using information regarding said marking in the course of computer processing the image information.

18. A method as in claim 15 including displaying an image of the patient's anatomy, including an image of the selected portion of the aorta, derived from said digital image information, and manually marking a calcified portion of the aorta visible in the image, wherein the producing of aortic calcification information comprises using information regarding said marking in the course of computer processing the image information.

19. A method as in claim 15 in which the producing of aortic calcification information comprises treating as calcified a composite of non-contiguous parts of the aorta that meet selected criteria.

20. A method as in claim 15 including inputting additional information regarding clinical risk factors for the patient and using said additional information in said estimating of cardiovascular risk information.

21. A method as in claim 15 including deriving bone assessment information by computer processing that uses said x-ray measurements, and wherein the reporting comprises showing the cardiovascular assessment information and the bone assessment information.

22. A method as in claim 21 in which the reporting comprises showing the cardiovascular risk information and the bone assessment information at different displays or documents.

23. A method as in claim 21 in which the reporting comprises showing the cardiovascular risk information and the bone assessment information concurrently.

24. A method as in claim 23 in which the reporting comprises showing the cardiovascular risk information and the bone assessment information at same display or document.

25. A method as in claim 15 including displaying information related to treatment guidelines related to the cardiovascular risk information.

26. A method as in claim 15 in which the obtaining of x-ray measurements comprises scanning the patient with a fan beam of x-rays.

27. A system comprising:
a dual x-ray energy range bone densitometer obtaining dual energy range x-ray measurements of a patient's anatomy that includes a selected portion of the patient's aorta;
a computer coupled with the densitometer and receiving said x-ray measurements therefrom, said computer being programmed to:
(a) process the x-ray measurements and thereby derive digital image information describing an image of at least the selected portion of the patient's aorta,
(b) process the digital image information and thereby produce aortic calcification information describing at least one selected calcification property of the selected portion of the aorta, and
(c) process the aortic calcification information and thereby estimate cardiovascular risk information related to an assessment of risk of a cardiovascular event for the patient; and
a display coupled with the computer and receiving said cardiovascular risk information therefrom and displaying an indication of a cardiovascular risk for the patient.

28. A system as in claim 27 wherein said computer is further programmed to process the digital image information and thereby calculate bone assessment information for the patient.

29. A system as in claim 28 wherein said display is coupled with said computer to receive the bone assessment information therefrom and displays an indication of the bone assessment information.

30. A system as in claim 28 in which said bone assessment information comprises bone fracture risk information.

31. A system as in claim 28 in which said bone assessment information comprises information related to at least one of bone mineral content and bone mineral density.

32. A system as in claim 21 in which said bone assessment information comprises bone fracture risk information.

33. A system as in claim 27 in which said digital image data comprises pixel values for respective pixels of a two-dimensional image of the patient's anatomy, and wherein said computer is programmed to carry out at least one pixel-based search algorithm in a process producing said aortic calcification information.

34. A system as in claim 27 in which said densitometer comprises a source of a fan-shaped beam of x-rays and a detector for x-rays traveling within respective sectors of said fan beam.

35. A computer readable medium carrying out one or more sequences of instructions stored therein in a non-transitory form, wherein execution of the one or more sequences of instructions by one or more processors causes the one or more processors to perform the steps of:
receiving at dual energy range x-ray measurements taken as a projection view of a patient's anatomy that includes a selected portion of the patient's aorta, said projection view having been taken at a substantially lower x-ray dose to the patent than a radiography or a CT slice-based image of the same anatomy;
processing the x-ray measurements to derive digital image information describing an image of at least the selected portion of the patient's aorta,
processing the digital image information to produce aortic calcification information describing at least one selected calcification property of the selected portion of the aorta,
processing the aortic calcification information to estimate cardiovascular risk information related to an assessment of risk of a cardiovascular event for the patient; and
displaying an indication of the estimated cardiovascular risk for the patient.

36. A computer readable medium as in claim 35 in which said x-ray measurements are taken in a lateral view of the patient.

37. A computer readable medium as in claim 35 in which said processing further comprises using said x-ray measurements to derive bone assessment information and said displaying further comprises displaying the bone assessment information.

38. A computer readable medium as in claim 37 in which said bone assessment information comprises bone fracture risk assessment information.

39. A computer readable medium as in claim 37 in which said bone assessment information comprises information related to at least one of bone mineral content and bone mineral density.

40. A computer readable medium as in claim 37 in which said digital image data comprises pixel values for respective pixels of a projection image of the patient's anatomy, and said processing comprises applying at least one pixel-based search algorithm in a process producing said aortic calcification information.

* * * * *